US008065008B2

(12) United States Patent
Sommer et al.

(10) Patent No.: US 8,065,008 B2
(45) Date of Patent: Nov. 22, 2011

(54) MULTI-POLAR ELECTRICAL MEDICAL LEAD CONNECTOR SYSTEM

(75) Inventors: John L. Sommer, Coon Rapids, MN (US); Douglas S. Hine, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 476 days.

(21) Appl. No.: 10/646,899

(22) Filed: Aug. 21, 2003

(65) Prior Publication Data
US 2005/0043771 A1 Feb. 24, 2005

(51) Int. Cl.
*A61N 1/375* (2006.01)
(52) U.S. Cl. .......................................... 607/37
(58) Field of Classification Search .................. 607/37, 607/36, 38; 439/909, 312, 322
See application file for complete search history.

(56) References Cited

U.S. PATENT DOCUMENTS

| | | | |
|---|---|---|---|
| 4,142,532 A | 3/1979 | Ware | 128/419 P |
| 4,182,345 A | 1/1980 | Grose | 128/419 P |
| 4,469,104 A * | 9/1984 | Peers-Trevarton | 607/27 |
| 4,583,543 A | 4/1986 | Peers-Trevarton | 128/419 P |
| 4,628,934 A * | 12/1986 | Pohndorf et al. | 607/27 |
| 5,000,177 A | 3/1991 | Hoffmann et al. | 128/419 P |
| 5,007,864 A | 4/1991 | Stutz, Jr. | 439/651 |
| 5,050,602 A | 9/1991 | Osypka | 128/419 P |
| 5,060,649 A | 10/1991 | Hocherl et al. | 128/419 P |
| 5,070,605 A | 12/1991 | Daglow et al. | 29/842 |
| 5,174,288 A | 12/1992 | Bardy et al. | 128/419 D |
| 5,235,978 A * | 8/1993 | Hirschberg et al. | 607/5 |
| 5,325,584 A | 7/1994 | Jasch | 29/876 |
| 5,328,442 A | 7/1994 | Levine | 600/17 |
| 5,374,279 A | 12/1994 | Duffin, Jr. et al. | 607/5 |
| 5,423,873 A | 6/1995 | Neubauer et al. | 607/68 |
| 5,613,858 A | 3/1997 | Estes et al. | 439/46 |
| 5,679,026 A * | 10/1997 | Fain et al. | 439/651 |
| 5,766,042 A | 6/1998 | Ries et al. | 439/668 |
| 5,843,141 A * | 12/1998 | Bischoff et al. | 607/37 |
| 6,044,302 A | 3/2000 | Persuitti et al. | 607/37 |
| 6,295,475 B1 | 9/2001 | Morgan | 607/122 |
| 6,755,694 B2 * | 6/2004 | Ries et al. | 439/668 |
| 2002/0115343 A1 | 8/2002 | Sommer et al. | 439/578 |
| 2004/0260355 A1* | 12/2004 | Holleman et al. | 607/37 |
| 2005/0033371 A1* | 2/2005 | Sommer et al. | 607/37 |

OTHER PUBLICATIONS

Merriam-Webster Online Dictionary, www.webster.com, define: flange.*

* cited by examiner

*Primary Examiner* — Niketa Patel
*Assistant Examiner* — Alyssa M Alter
(74) *Attorney, Agent, or Firm* — Carol F. Barry

(57) ABSTRACT

A lead connector is terminated proximally by a connector pin and includes a circumferential array of connector pads, each connector pad coupled to an electrode via an elongated insulated conductor. A lumen of an adaptor is adapted to engage the lead connector and includes an electrical contact zone formed therein and positioned for coupling with a one of the array of connector pads, when the connector is engaged within the lumen, in order to facilitate electrical connection of a selected electrode corresponding to the one of the array of connector pads.

18 Claims, 6 Drawing Sheets

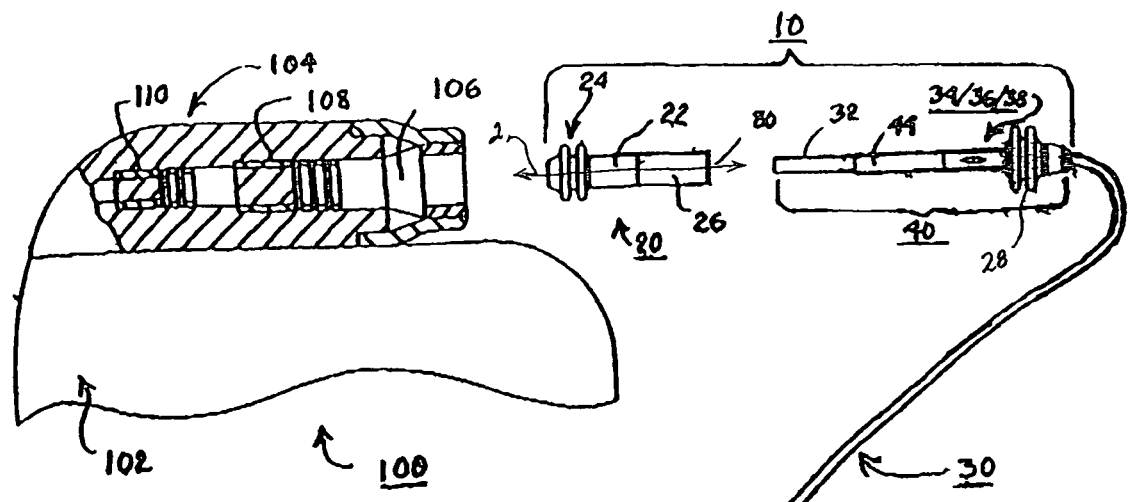
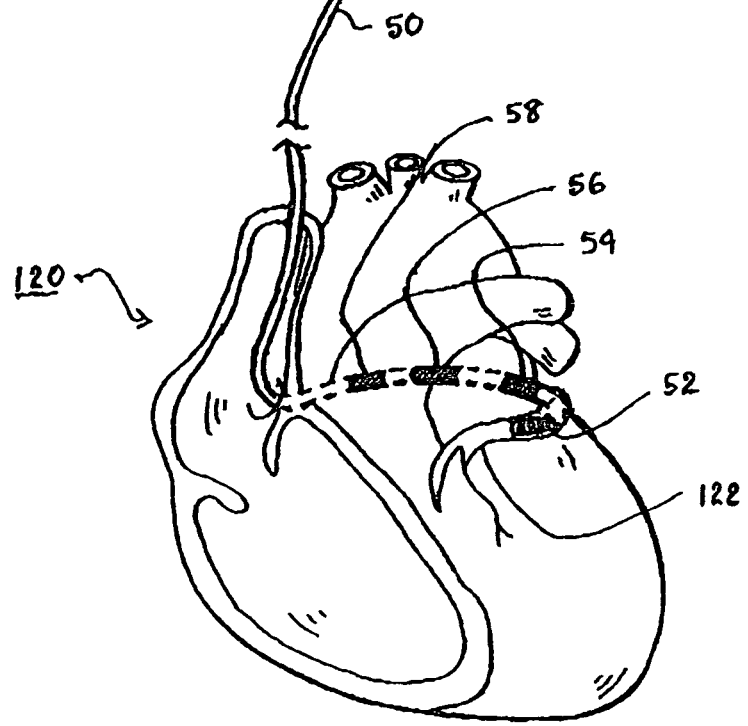
FIG. 1

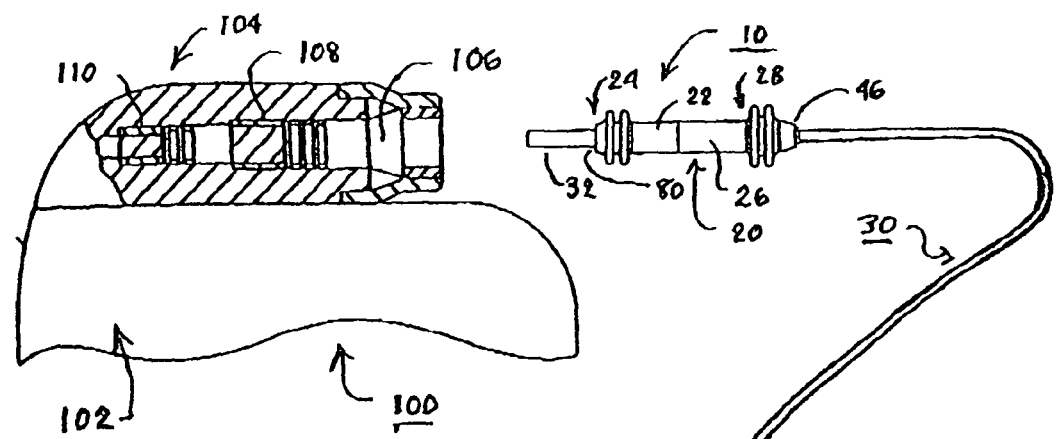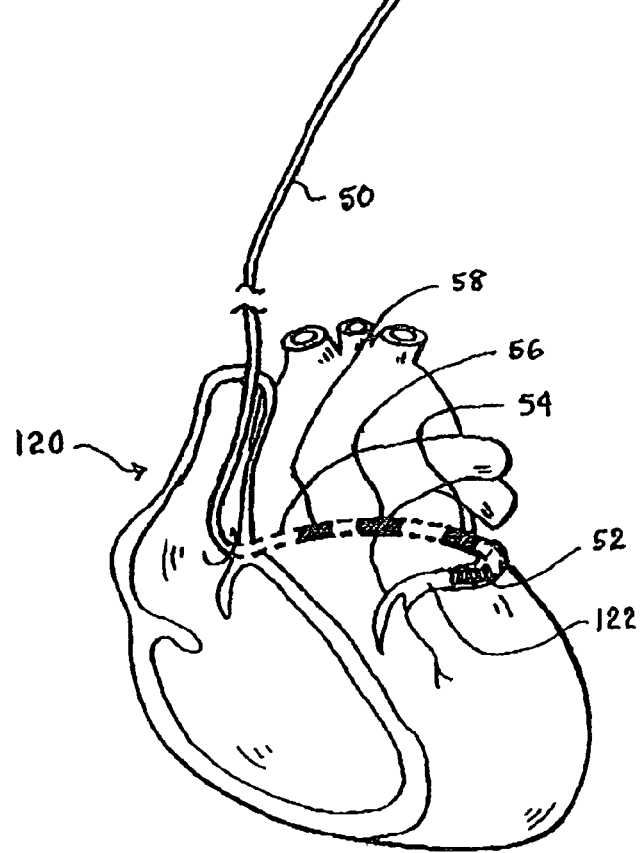
FIG. 2

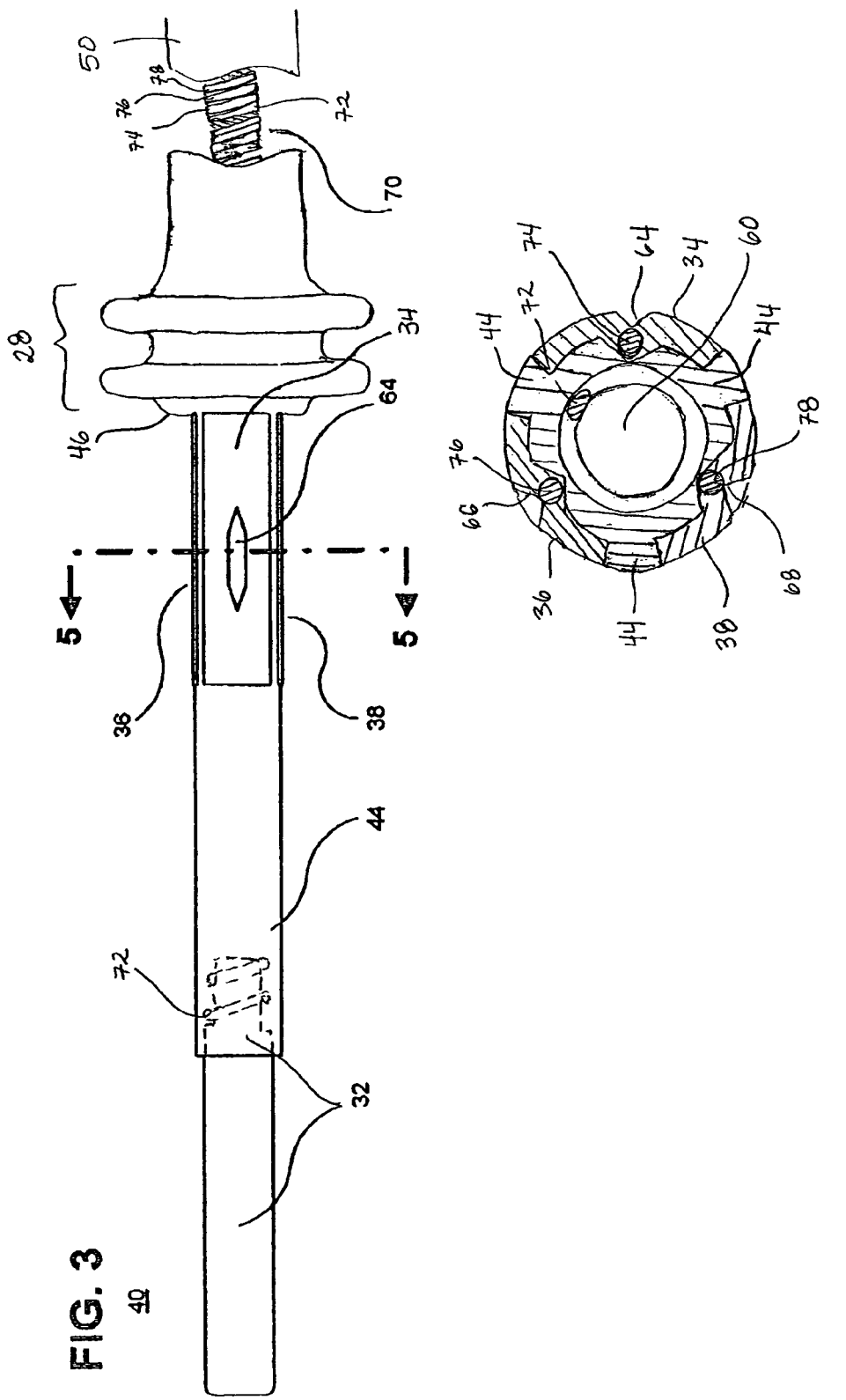

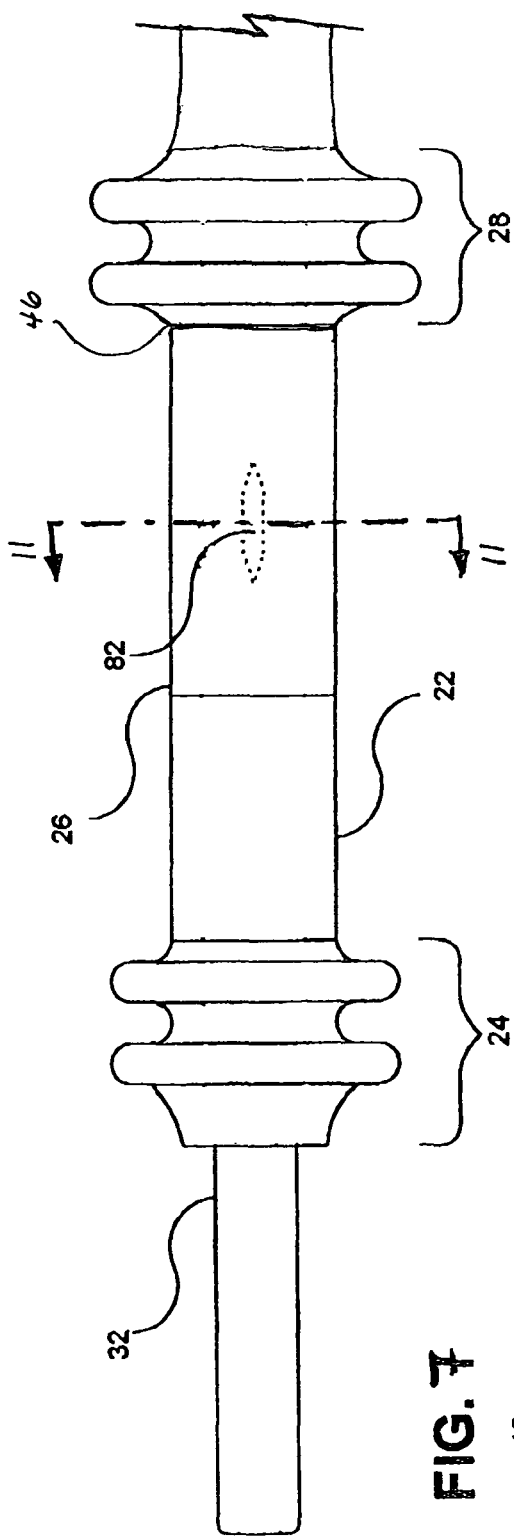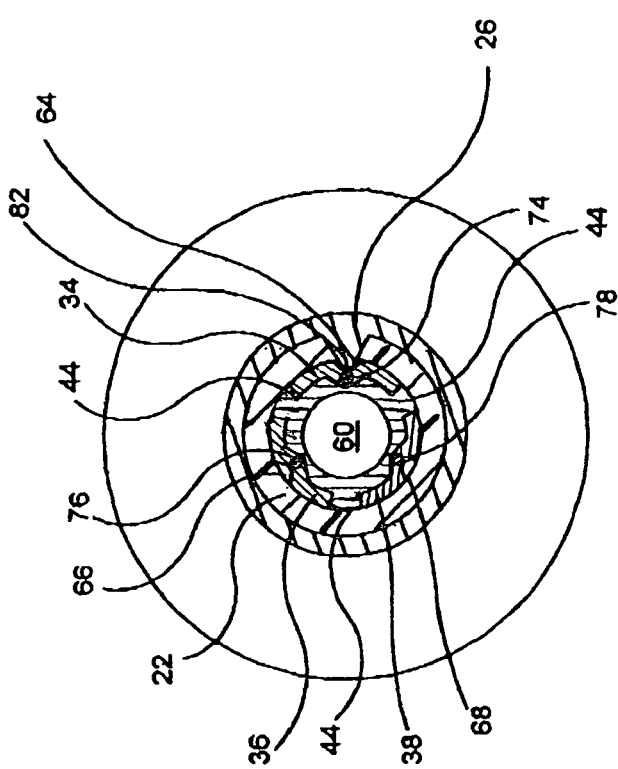

MULTI-POLAR ELECTRICAL MEDICAL LEAD CONNECTOR SYSTEM

CROSS-REFERENCE TO RELATED APPLICATION

Cross-reference is hereby made to the following commonly assigned related U.S. Applications: application Ser. NO. 10/646,545 to Douglas Hine et al., filed concurrently herewith, entitled MULTI-POLAR ELECTRICAL MEDICAL LEAD CONNECTOR SYSTEM.

FIELD OF THE INVENTION

Embodiments of the present invention relate to implantable medical device connectors and more particularly to a connection system adapted to allow selection of one or more electrodes from a plurality of electrodes included on a medical electrical lead for permanent connection with the medical device.

BACKGROUND OF THE INVENTION

Implantable medical electrical stimulation and/or sensing leads are well known in the fields of cardiac stimulation and monitoring, including cardiac pacing and cardioversion/defibrillation, and in other fields of electrical stimulation or monitoring of electrical signals or other physiologic parameters. In the field of cardiac stimulation and monitoring, endocardial leads are placed through a transvenous route to locate one or more stimulation and/or sense electrodes, along or at the distal end of the lead body, in a desired location within a chamber of the heart or within a blood vessel of the heart. Epicardial leads are routed from a subcutaneous site to dispose one or more stimulation and/or sense electrodes, along or at the distal end of the lead body, at an epicardial site on the heart. A pacemaker implantable pulse generator (IPG) or implantable cardioverter/defibrillator (ICD) or monitor, referred to herein generically as an implantable medical device (IMD) is coupled to the heart through one or more of such endocardial or epicardial leads forming medical system. Means for implanting such cardiac leads are known to those skilled in the art of pacing and defibrillation therapy.

Proximal ends of such cardiac leads typically are formed with a lead connector assembly that is inserted into a connector bore of a connector block of the IPG or monitor. The lead body extending distally from the connector assembly typically includes one or more insulated conductors surrounded by an outer insulative sheath. Each conductor couples a lead connector contact of the lead connector assembly with a distal stimulation and/or sense electrode.

More recently, medical electrical leads have been constructed with an array of pacing and/or sensing electrodes from which one or more electrodes may be selected to optimize electrical stimulation therapy and/or monitoring. One example of such a lead is a coronary vein lead implanted to stimulate a left atrium or left ventricle; other examples include a right atrial or ventricular lead implanted to stimulate an endocardial portion of the right atrium or ventricle or leads implanted to stimulate directly a portion of the cardiac conduction system. A connection system for these types of leads needs to be adapted for the selection of one or more electrodes included in the array.

BRIEF DESCRIPTION OF THE DRAWINGS

Embodiments of the present invention will be more readily understood from the following detailed description when considered in conjunction with the drawings, in which like reference numerals indicate identical structures throughout the several views, and wherein:

FIG. 1 is a schematic depicting an IMD in part in relation to an adaptor and a connector of a cardiac lead according to one embodiment of the present invention;

FIG. 2 is a schematic depicting the IMD of FIG. 1 in part relation to the connector of FIG. 1 inserted into the adaptor of FIG. 1;

FIG. 3 is an enlarged plan view with a partial cut-away section of the connector shown in FIG. 1 according to one embodiment of the present invention.

FIG. 4 is a radial section view through section line 5-5 of FIG. 3.

FIG. 7 is plan view of an adaptor fitted over a lead connector according to embodiments of the present invention;

FIG. 8 is a radial section through section line 11-11 of FIG. 7 showing an interface between the lead connector and adaptor according to one embodiment of the present invention.

DETAILED DESCRIPTION OF THE INVENTION

Figure 6:
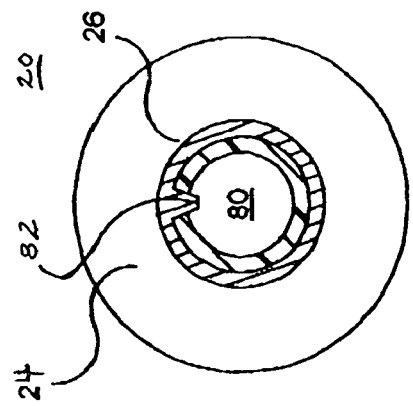
FIG. 6 is a radial section view through section line 9-9 of FIG. 5.

In the following detailed description, references are made to illustrative embodiments of the invention. The embodiments are described in the context of a pacing system incorporated in an implantable pacemaker or ICD comprising an ICD or pacemaker IPG (herein collectively referred to as an IMD) and at least one cardiac lead. It will be understood that more than one cardiac lead can be coupled to the IMD connector and extend to the heart in a manner well known in the art. It will be understood that the present invention can be incorporated into other medical electrical leads coupled to other IMD's through adaptors incorporating the principles of the present invention for delivering electrical stimulation elsewhere in the body. It is therefore understood that other embodiments can be utilized without departing from the scope of the invention.

Moreover, adaptors according to the present invention, when assembled with a lead connector may conform to an industry standard for IMD lead connectors; however, it is not necessary to the practice of the invention that the assembly conform to an existing industry standard. Moreover, the degree to which an adaptor of the present invention "up-sizes" the lead connector can range from a negligible up-sizing to a significant up-sizing without departing from the practice of the invention.

FIG. 1 is a schematic depicting an IMD 100 in part in relation to an adaptor 20 and a connector 40 of a cardiac lead according to one embodiment of the present invention and FIG. 2 is a schematic depicting IMD 100 in part relation to connector 40 inserted into the adaptor 20 forming an assembly 10. FIG. 1 illustrates connector 40 terminating a proximal end of a cardiac lead 30 and including a set of sealing rings 28 and a plurality of lead connector elements including a proximal connector pin 32 an array of lead connector pads 34, 36, 38 circumferentially electrically separated and spaced apart by segments of an insulator 44; connector pads 34, 36, 38 are arcuate or substantially planar or flattened according to alternate embodiments. According to one embodiment, connector pin 32 is coupled via an elongated lead conductor to a distal tip pace/sense electrode 52 and each of the plurality of lead connector pads 34, 36, 38 are coupled via elongated lead conductors extending through lead body 50 to respective distally located pace/sense electrodes 54, 56, 58 spaced apart along lead body 50 in a distal segment thereof; one of pace/sense electrodes 54, 56, 58 implanted in proximity to particular pace/sense sites is selected for delivery of pacing pulses and/or sensing of the electrical signals of a heart in conjunction with electrode 52. For example, FIGS. 1 and 2 illustrate cardiac lead 30 implanted in a coronary sinus (CS) of a heart 120 and adaptor 20 is used to select one of the plurality of pace/sense electrodes 54, 56, 58, which are positioned within a vein 122 branching from the CS. According to alternate embodiments connector pin 32 is coupled to one of electrodes 54, 56, 58 and each of the plurality of connector pads 34, 36, 38 are coupled to distal tip electrode 52 and each remaining electrode of electrodes 54, 56, 58, from which one is selected by adaptor 20.

As further illustrated in FIG. 1, adaptor 20 includes an elongated electrically insulating, tubular adaptor body 22 extending distally from a set of proximal sealing rings 24 and supporting a connector ring 26. According to embodiments of the present invention, a lumen 80 of adaptor 20 is sized to receive connector 40 wherein connector ring 26 is internally configured to make electrical and mechanical contact with one of the array of connector pads 34, 36, 38; a selection of one of the array of connector pads 34, 36, 38 being made by rotating adaptor about a longitudinal axis 2, which will be described in detail below. Outer dimensions of assembly 10 of adaptor 20 positioned over connector 40, as illustrated in FIG. 2, are sized to sealingly mate with a connector bore 106 of IMD 100.

FIGS. 1 and 2 illustrate IMD 100 including a connector header 104 attached to a wall of a hermetically sealed enclosure 102 that encloses a battery and electronic circuitry and electrical and other components. Connector header 104 contains at least one connector bore 106 for receiving assembly 10 of adaptor 20 and connector 40. Connector header 104 supports two connector blocks 110 and 108 of any of the known types that are electrically connected to the electronic circuitry through feedthrough pins of feedthroughs (not shown) that are mounted to extend through the wall of the hermetically sealed enclosure 102. Inner diameters of connector blocks 110 and 108 are dimensioned and positioned in connector bore 106 to receive and make electrical and mechanical connection with connector pin 32 and connector ring 26, respectively, of assembly 10. The electrical and mechanical connection is effected typically through the tightening of setscrews (not shown) as disclosed in U.S. Pat. Nos. 4,142,532 and 4,182,345, for example, or the action of inwardly extending force beams (not shown) as disclosed in U.S. Pat. Nos. 5,070,605 and 5,766,042, for example; both of which are well known to those skilled in the art. According to embodiments of the present invention, assembly 10 is inserted into the connector bore 106, so that connector pin 32 and connector ring 26 are seated within the axially aligned bores of connector blocks 110 and 108, respectively. The setscrews and/or inwardly extending force beams apply force against connector pin 32 and compress the adaptor connector ring 26 against one of the array of connector pads 34, 36, and 38. It will be understood that the compression force advantageously traps lead connector 40 within the confines of adaptor lumen 80, and that assembly 10 is sealed from the environment by compression of sealing rings 24 and 28 within the IMD connector bore 106.

FIG. 3 is an enlarged plan view with a partial cut-away section of connector 40 according to one embodiment of the present invention and FIG. 4 is a radial section view through section line 5-5 of FIG. 3. FIGS. 3 and 4 illustrates array of connector pads 34, 36, 38 including surface depressions 64, 66, 68, respectively, and mounted upon insulating sleeve 44 which extends from sealing rings 28 to connector pin 32; outward protrusions of insulating sleeve 44 electrically separate the adjacent elongated edges of connector pads 34, 36, 38. Means for joining insulating sleeve 44, connector pin 32, connector pads 34, 34, 38, and sealing rings 28 to form connector 40 include insert molding, mechanical interlocks, adhesive bonds, any combination thereof, and/or other methods well known in the art of lead construction. The relative widths of connector pads 34, 36, 38 and the protrusions of insulating sleeve 44 extending between connector pads 34, 36, 38 can be selected in any desired ratio. According to embodiments of the present invention, depressions 64, circumferentially spaced at approximately 120° from one another, as illustrated in FIG. 4, are elongated axially, as shown, elongated radially or formed in circular dimples; in any such configuration, the slot sides can be ramped.

FIGS. 3 and 4 further illustrate an embodiment of lead 30 wherein the conductors are insulated wires 72, 74, 76, and 78 wound to form of a multi-filar coil 70 including a lumen 60; junctions between wires 72, 74, 76, and 78 and respective distal electrodes 52, 54, 56 and 58 (FIGS. 1 and 2) are formed by crimps, welds, stakes, or other joining means well known to those skilled in the art of lead construction. A proximal end of conductor 72 shown in part by phantom lines extends to lead connector pin 32, also shown by phantom lines within insulating sleeve 44, where it is joined thereto by welding, crimping, staking or other means well known in the art. Proximal ends of conductors 74, 76, and 78 each extend into respective bores of or against inner surfaces of respective connector pads 34, 36, 38 where junctions are formed by welding, crimping, staking or any other means well known in the art. In alternate embodiments any combination of wound wire conductors and cable conductors may be incorporated into lead 30, means by which are well known to those skilled in the art of lead construction.

Figure 5:
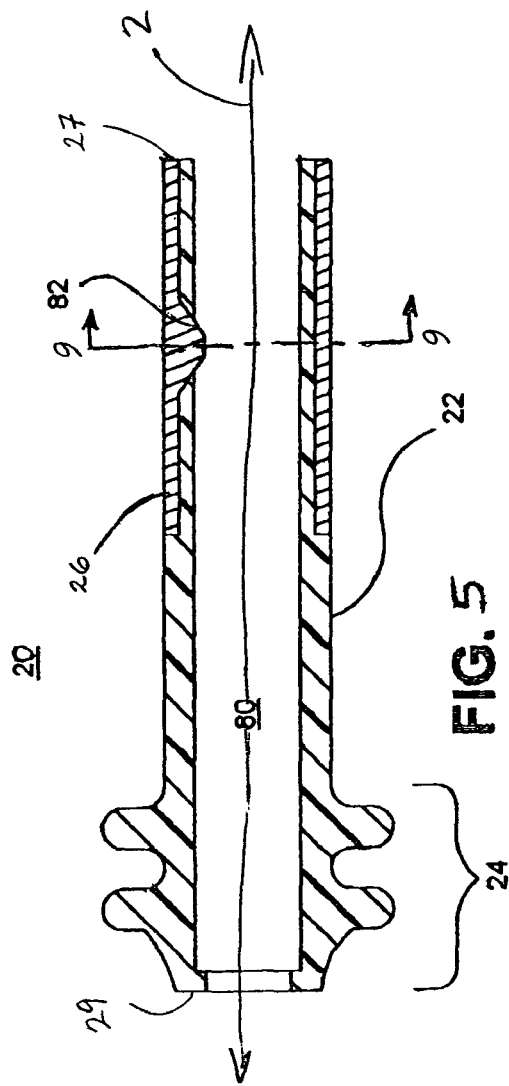
FIG. 5 is an enlarged plan view of the adaptor shown in FIGS. 1 and 2 according to one embodiment of the present invention.

FIG. 5 is an enlarged plan view of adaptor 20 according to one embodiment of the present invention and FIG. 6 is a radial section view through section line 9-9 of FIG. 5. FIGS. 5 and 6 illustrate connector ring 26 of adaptor 20 including a key 82 extending inward through insulating adaptor body 22 to function as an electrical contact for coupling with a selected connector pad from the array of connector pads 34, 34, 38 (FIGS. 3 and 4) when connector 40 is inserted within lumen 80. Lead connector 40 is manually inserted into adaptor lumen 80 until a stop 46 (FIG. 3) abuts a distal end 27 of adaptor and connector pin 32 protrudes from a proximal end 29 of adaptor 20 as illustrated in FIG. 7. FIG. 7 is plan view of adaptor 20 fitted over lead connector 40 according to embodiments of the present invention and FIG. 8 is a radial section through section line 11-11 of FIG. 7 showing an interface between key 82 and connector pad 34 according to one embodiment of the present invention. According to embodiments of the present invention, in order to select a connector pad from the array of pads 34, 36, 38, adaptor 20 is rotated about longitudinal axis 2 (FIG. 5) such that key 82 is aligned with the selected connector pad upon insertion of connector 40 within lumen 80, for example connector pad 34 illustrated in FIG. 9.

According to one embodiment, inwardly extending key 82 is resilient and formed like a force beam, which "gives" in the outward direction when force is applied by insertion of connector 40. The inwardly extending key 82 can be elongated axially, as shown, ball-shaped like a detent ball, or elongated circumferentially, a form dictated only by that of mating surfaces of connector pads formed on a lead connector, for example pads 34, 36, 38, in order to facilitate stable electrical contact between key 82 and connector pads. Furthermore, a mechanical interlock between key 82 and the selected pad of pads 34, 36, 38 may be formed, for example with surface depressions 64, 66, 68, which may create either a permanent or reversible junction between adaptor 20 and connector 40 when connector 40 is fully engaged within lumen 80 of adaptor 20.

Figure 9:
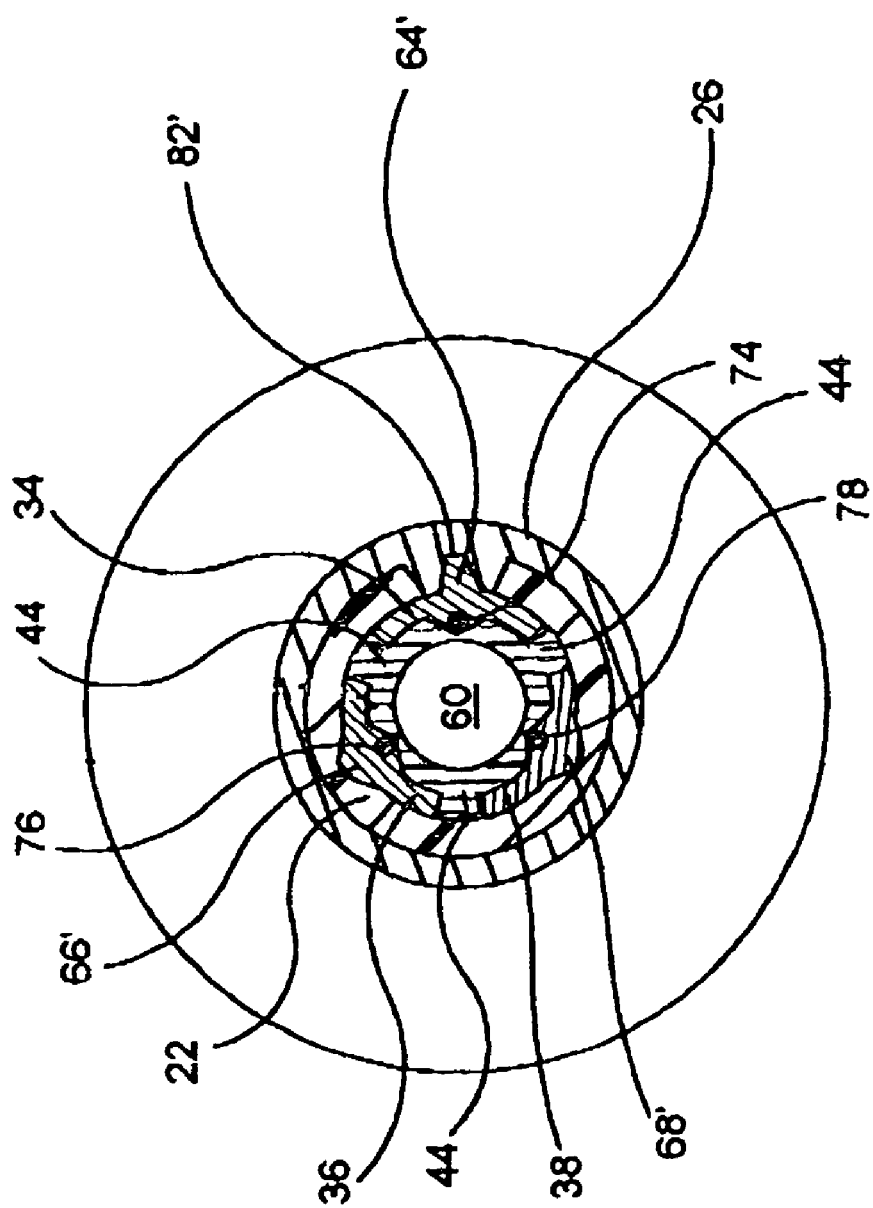
FIG. 9 is a radial section through section line 11-11 of FIG. 7 showing an interface between the lead connector and adaptor according to an alternate embodiment of the present invention.

Although the above-described embodiments depict the key 82 extending inwardly from the adaptor connector ring for engagement within of the depressions 64, 66, and 68, it will be understood that the relative configuration can be reversed as illustrated in FIG. 9. FIG. 9 is a radial section through section line 11-11 of FIG. 7 showing an interface between connector pad 34 and key 82 wherein lead connector pads 34, 36, and 38 are formed having outwardly extending resilient protrusions 64, 66, 68 to engage a depression within key 82. According to additional alternate embodiments, key 82 is disposed in a keyway cut through the adaptor connector ring 26 so that lead connector may be inserted into lumen 80, adaptor may be rotated to position the keyway over a selected connector pad and then key 82 can then be driven inward to engage the selected connector pad.

It should be understood that, while specific embodiments have been presented in the foregoing detailed description of the invention, a vast number of variations exist. It should also be appreciated that the exemplary embodiments are only examples, and are not intended to limit the scope, applicability, or configuration of the invention in any way. For example, four connector pads can be disposed circumferentially around the lead body circumferentially spaced at about 90° from one another; six arcuate connector pads can be disposed circumferentially around the lead body circumferentially spaced at about 60° from one another, etc.

Moreover, it will be understood that the IMD connector bore can be configured to accept a tripolar lead as disclosed in the above-referenced '042 patent. In that instance, electrical medical lead 30 may have first and second connector pad arrays positioned along and each extending circumferentially around connector 40. A bipolar adaptor would include first and second spaced apart adaptor connector rings adapted to make contact with selected ones of the connector pads of the respective first and second connector pad arrays. Still further, it will be understood that further adaptors may be devised that select more than one of the distal electrodes coupled to the lead connector pads.

It will be understood that certain of the above-described structures, functions and operations of the above-described embodiments are not necessary to practice the present invention and are included in the description simply for completeness of an exemplary embodiment or embodiments.

In addition, it will be understood that specifically described structures, functions and operations set forth in the above-referenced patents can be practiced in conjunction with the present invention, but they are not essential to its practice.

It is therefore to be understood, that within the scope of the appended claims, the invention may be practiced otherwise than as specifically described without actually departing from the spirit and scope of the present invention.

What is claimed is:

1. A medical device lead connector system comprising:
   a connector header including a connector bore, the connector bore having an inner bore surface;
   a lead having a lead body, a plurality of elongated insulated conductors extending within the lead body between a plurality of lead electrodes at a lead body distal end and a lead connector at a lead body proximal end, wherein the lead connector extends along a longitudinal axis and includes:
      an array of lead connector pads, wherein the pads are distributed circumferentially in an adjacent spaced apart relationship around a periphery of the lead connector such that a plane perpendicular to the longitudinal axis of the lead connector intersects with more than one of the lead connector pads of the array of lead connector pads, and
      a connector pin proximal of the array of lead connector pads, the connector pin being coupled to one of the plurality of lead electrodes, and each of the lead connector pads being coupled to an individual one of the other of the plurality of lead electrodes; and
   an adaptor comprising:
      an insulating adaptor body having a proximal end and a distal end;
      a lumen within the adaptor body having an inner lumen surface extending from a proximal end to a distal end and dimensioned to receive the lead connector for relative rotational movement therein, and
      a connector ring extending circumferentially over a segment of an exterior surface of the adaptor body and shaped to form an electrical contact resilient key along an inner portion of the connector ring extending through the insulating adaptor body into the lumen to project from the inner lumen surface, the key dimensioned so as to be in registration with a selected one of the lead connector pads at a time when the lead connector is inserted into the lumen of the adaptor body and rotated relative to the adaptor body about a longitudinal axis extending from the proximal end of the insulating adaptor body to the distal end of the insulating adapter adaptor body so as to be in alignment with the selected lead connector pad;
   wherein registration of the key with a selected one of the lead connector pads at a time provides for lead electrode array selectivity; and
   wherein the insulating adaptor body is dimensioned to be received within the connector bore of the connector header.

2. The medical device lead connector system of claim 1, wherein the external surface configuration of the insulating adaptor body conforms to an industry standard.

3. The medical device lead connector system of claim 1, wherein the external surface of the adaptor body conforms to an industry standard.

4. The medical device lead connector system of claim 1, wherein the external surface of the adaptor body further includes a set of sealing rings positioned proximal to the conductive surface.

5. The medical device lead connector system of claim 1, wherein the lead connector further includes a plurality of sealing rings positioned distal to the plurality of connector pads.

6. The medical device lead connector system of claim 1, wherein the lead connector further includes a mechanical stop to engage the distal end of the adaptor body when the lead connector is fully inserted within the lumen of the adaptor body.

7. The medical device lead connector system of claim 1, wherein the key is a resilient force beam.

8. The medical device lead connector system of claim 1, wherein each connector pad includes a surface depression adapted to mate with the key.

9. A medical device lead connector system comprising:
  a connector header including a connector bore, the connector bore having an inner bore surface;
  a lead having a lead body, a plurality of elongated insulated conductors extending within the lead body between a plurality of lead electrodes at a lead body distal end and a lead connector at a lead body proximal end, wherein the lead connector extends along a longitudinal axis and includes:
    an array of lead connector pads, wherein the pads are distributed circumferentially in an adjacent spaced apart relationship around a periphery of the lead connector such that a plane perpendicular to the longitudinal axis of the lead connector intersects with more than one of the lead connector pads of the array of lead connector pads, and
    a connector pin proximal of the array of lead connector pads, the connector pin being coupled to one of the plurality of lead electrodes, and each of the lead connector pads being coupled to an individual one of the other of the plurality of lead electrodes, wherein each connector pad includes a resilient protrusion extending radially from the periphery of the lead connector; and
  an adaptor comprising:
    an insulating adaptor body having a proximal end and a distal end;
    a lumen within the adaptor body having an inner lumen surface extending from a proximal end to a distal end and dimensioned to receive the lead connector for relative rotational movement therein, and
    a connector ring extending circumferentially over a segment of an exterior surface of the adaptor body and shaped to form a surface depression along an inner portion of the connector ring, the depression dimensioned so as to be in registration with the protrusion of a selected one of the lead connector pads at a time when the lead connector is inserted into the lumen of the adaptor body and rotated relative to the adaptor body about a longitudinal axis extending from the proximal end of the insulating adaptor body to the distal end of the insulating adaptor body so as to be in alignment with the selected lead connector pad;
  wherein registration of the depression with the protrusion of a selected one of the lead connector pads at a time provides for lead electrode array selectivity; and
  wherein the insulating adaptor body is dimensioned to be received within the connector bore of the connector header.

10. A method for optimizing implantable medical device electrical stimulation therapy using a lead having a plurality of selectively active lead electrodes, comprising:
  providing a lead connector at the proximal end of the lead, the lead connector extending along a longitudinal axis and including an array of individual, circumferentially distributed lead connector pads such that a plane perpendicular to the longitudinal axis of the lead connector intersects with more than one of the lead connector pads, and a connector pin proximal of the array of lead connector pads, wherein the connector pin is coupled to one of the plurality of lead electrodes and each of the individual, circumferentially distributed lead connector pads being coupled to an individual one of the other of the plurality of lead electrodes;
  providing an adaptor, the adaptor comprising an insulating adaptor body having a proximal end and a distal end, a lumen within the adaptor body having an inner lumen surface extending from a proximal end to a distal end and dimensioned to receive the lead connector for relative rotational movement therein, a connector ring extending circumferentially over a segment of an exterior surface of the insulating adaptor body and shaped to form an electrical contact resilient key along an inner portion of the connector ring and extending through the insulating adaptor body into the lumen to project from the inner lumen surface, the key being dimensioned to be in registration with one of the individual, circumferentially distributed lead connector pads at a time when the lead connector is inserted into the lumen of the adaptor body and rotated relative to the adaptor body to align with any one of the plurality of lead connector pads;
  inserting the lead connector within the adaptor lumen; and
  rotating the adaptor about an axis extending through the adaptor to selectively align the key of the adaptor in registration with one of the lead connector pads and thereby select the lead connector pad and thereby permit selective activation of one of the lead electrodes, wherein lead electrode array selectivity is provided.

11. The method of claim 10, further comprising the step of inserting the adaptor into a connector header bore of an implantable medical device to electrically couple the selected lead connector pad to the implantable medical device.

12. A medical device lead connector system for coupling a lead to a medical device, wherein the medical device comprises a connector bore defining an inner surface, wherein the system comprises:
  a lead connector extending from a proximal end to a distal end along a longitudinal axis, wherein the lead connector comprises a plurality of connector pads electrically isolated from one another and distributed circumferentially around an outer surface of the lead connector such that a plane perpendicular to the longitudinal axis of the lead connector intersects with more than one of the plurality of connector pads; and
  an adaptor configured to be received within the connector bore of the medical device, wherein the adaptor comprises:
    a body comprising insulative material and extending from a proximal end to a distal end, wherein the body comprises a lumen defining an inner lumen surface and extending from the proximal end to the distal end, wherein the lumen is configured to receive the lead connector, and
    an electrical connector along an outer surface of the body configured to be electrically coupled to a conductive portion of the inner surface of the connector bore of the medical device when the adaptor is received therein, wherein the electrical connector comprises a electrical contact key along the inner lumen surface of the lumen of the body, wherein the electrical contact key is configured to contact a selected connector pad of the plurality of connector pads to electrically couple the electrical connector of the adaptor to the selected connector pad of the lead connector when the lead connector is received within the lumen of the body of the adaptor, wherein the lead connector is configured to be rotatable about the longitudinal axis when the lead connector is received within the lumen of the body of the adaptor to select any one lead connector pad of the plurality of lead connector pads to be contacted by the electrical contact key of the electrical connector of the adaptor.

13. The system of claim 12, wherein the insulative material of the body of the adaptor is configured to contact the plurality of connector pads other than the selected connector pad to electrically isolate the plurality of connector pads other than the selected connector pad.

14. The system of claim 12, wherein the electrical connector comprises a connector ring.

15. The system of claim 12, wherein the lead connector further comprises a connector pin located proximally to the plurality of connector pads and configured to extend through the lumen of the body of the adaptor beyond the proximal end of the body of the adaptor when the lead connector is received within the lumen of the body of the adaptor.

16. The system of claim 12, wherein the electrical contact key of the electrical connector extends into the lumen of the body of the adaptor, and wherein each connector pad of the plurality connector pads defines a surface depression configured to receive the electrical contact key of the electrical connector of the adaptor when the lead connector is received within the lumen of the body of the adaptor.

17. The system of claim 12, wherein each connector pad of the plurality connector pads comprises a protrusion extending radially from the outer surface of the lead connector, and wherein the electrical contact key of the electrical connector defines a depression configured to receive the protrusion of the selected connector pad of the plurality of connector pads when the lead connector is received within the lumen of the body of the adaptor.

18. A method of electrical coupling an electrode of a lead to a medical device using an adaptor, wherein lead comprises a plurality of electrodes, wherein the adaptor comprises a body comprising a lumen defining an inner lumen surface and a electrical connector along an outer surface of the body, wherein the electrical connector comprises a electrical contact key along the inner lumen surface of the lumen of the body, wherein the method comprises:

providing a lead connector located on the proximal end of the lead, wherein the lead connector extends along a longitudinal axis and comprises a plurality of connector pads electrically isolated from one another and distributed circumferentially around an outer surface of the lead connector such that a plane perpendicular to the longitudinal axis of the lead connector intersects with more than one of the plurality of connector pads, wherein each of the plurality of connector pads is electrically coupled to a different electrode of the plurality of electrodes of the lead than the other connector pads;

selecting an electrode of the plurality electrodes of the lead by rotating the lead connector and the adaptor about the longitudinal axis relative each other such that the electrical contact key of the electrical connector of the adaptor is aligned with the connector pad of the plurality of connector pads corresponding to the selected electrode; and inserting the lead connector into the lumen of the adaptor after selecting the electrode.

* * * * *